(12) United States Patent
Bland et al.

(10) Patent No.: US 9,000,160 B2
(45) Date of Patent: Apr. 7, 2015

(54) PROCESS FOR THE PREPARATION OF 2-AMINO-5,8-DIMETHOXY [1,2,4]TRIAZOLO[1,5-C]PYRIMIDINE FROM 4-CHLORO-2,5-DIMETHOXYPYRIMIDINE

(71) Applicants: Douglas C. Bland, Midland, MI (US); Gary Roth, Midland, MI (US); Craig Bott, Clare, MI (US); Christopher T. Hamilton, Midland, MI (US); Joseph Neuman, Midland, MI (US)

(72) Inventors: Douglas C. Bland, Midland, MI (US); Gary Roth, Midland, MI (US); Craig Bott, Clare, MI (US); Christopher T. Hamilton, Midland, MI (US); Joseph Neuman, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/022,766

(22) Filed: Sep. 10, 2013

(65) Prior Publication Data

US 2014/0081023 A1    Mar. 20, 2014

Related U.S. Application Data

(60) Provisional application No. 61/701,250, filed on Sep. 14, 2012.

(51) Int. Cl.
| | | |
|---|---|---|
| C07D 487/00 | (2006.01) | |
| C07D 239/02 | (2006.01) | |
| C07D 487/04 | (2006.01) | |
| C07D 239/52 | (2006.01) | |

(52) U.S. Cl.
    CPC ............ *C07D 487/04* (2013.01); *C07D 239/52* (2013.01)

(58) Field of Classification Search
    None
    See application file for complete search history.

(56) References Cited

U.S. PATENT DOCUMENTS

| 6,005,108 A | 12/1999 | Johnson et al. |
| 6,362,335 B2 | 3/2002 | Roth et al. |

*Primary Examiner* — Jeffrey H Murray
(74) *Attorney, Agent, or Firm* — Michael R. Asam

(57) ABSTRACT

2-Amino-5,8-dialkoxy[1,2,4]-triazolo[1,5-c]pyrimidines are manufactured from 4-chloro-2,5-dialkoxypyrimidines in a process that avoids hydrazine and cyanogen halide.

21 Claims, No Drawings

PROCESS FOR THE PREPARATION OF 2-AMINO-5,8-DIMETHOXY[1,2,4]TRIAZOLO[1,5-C]PYRIMIDINE FROM 4-CHLORO-2,5-DIMETHOXYPYRIMIDINE

CROSS REFERENCE TO RELATED APPLICATIONS

This application claims the benefit of U.S. Provisional Patent Application Ser. No. 61/701,250 filed Sep. 14, 2012, the disclosure of which is expressly incorporated herein by reference.

BACKGROUND

Provided herein are processes for the preparation of 2-amino-5,8-dimethoxy[1,2,4]triazolo[1,5-c]pyrimidine from 4-chloro-2,5-dimethoxypyrimidine.

U.S. Pat. No. 6,005,108 describes certain substituted 2-amino-5,8-dialkoxy[1,2,4]-triazolo[1,5-c]pyrimidine compounds and their use as intermediates for the preparation of sulfonamide herbicides. 2-Amino-5,8-dimethoxy[1,2,4]triazolo[1,5-c]pyrimidine is a useful intermediate for the preparation of penoxsulam. Monatsh. Chem. 1983, 114, 789 describes the preparation of certain (amino)carbonothioylcarbamates followed by their reaction with hydroxylamine and subsequent cyclization to [1,2,4]triazolo[1,5-a]pyrimidin-2-amines. WO 2009/047514 A1 describes the preparation of certain (amino)carbonothioylcarbamates followed by their reaction with hydroxylamine and subsequent cyclization to [1,2,4]triazolo[1,5-a]pyridine and [1,2,4]triazolo[1,5-c]pyrimidine compounds. U.S. Pat. No. 6,559,101 B2 describes the preparation of certain (amino)carbonothioylcarbamates followed by their reaction with hydroxylamine and subsequent cyclization to pyrimidine-substituted [1,2,4]triazolo[1,5-a]pyrimidin-2-amines.

U.S. Pat. No. 6,362,335 B2 describes the production of 2-amino-5,8-dimethoxy[1,2,4]-triazolo[1,5-c]pyrimidine from 2,4-dichloro-5-methoxypyrimidine or 4-chloro-2,5-dimethoxypyrimidine in a multistep process that involves both hydrazine and a cyanogen halide. Hydrazine presents a severe explosion hazard and is toxic by ingestion, inhalation and skin adsorption. It is classified as a carcinogen and has a threshold limit value (TLV) of 0.1 ppm in air. Cyanogen halides are highly irritating and very poisonous. It would be advantageous to produce 2-amino-5,8-dialkoxy[1,2,4]triazolo[1,5-c]pyrimidines efficiently and in high yield by a manufacturing process that avoids hydrazine and cyanogen halide.

SUMMARY

Provided herein are processes for the preparation of 2-amino-5,8-dialkoxyl[1,2,4]-triazolo[1,5-c]pyrimidine from 4-chloro-2,5-dialkoxypyrimidines. More particularly, provided herein are processes for the preparation of 2-amino-5,8-dialkoxy[1,2,4]-triazolo[1,5-c]pyrimidines of the formula (I),

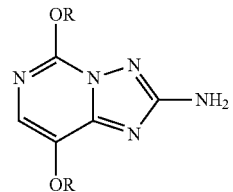

in which
R represents $C_1$-$C_4$ alkyl
which comprises:
i) contacting a 4-chloro-2,5-dialkoxypyrimidine of the formula

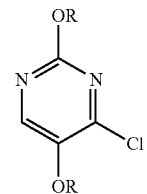

in which R is as previously defined
with a salt of cyanamide in a polar aprotic solvent to provide a 2,5-dialkoxy-4-cyanoaminopyrimidine of the formula

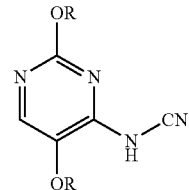

in which R is as previously defined;
ii) contacting the 2,5-dialkoxy-4-cyanoaminopyrimidine with either hydroxylamine as a free base or hydroxylamine salt in the presence of a base to provide a 2,5-dialkoxy-4-hydroxyguanidinylpyrimidine of the formula

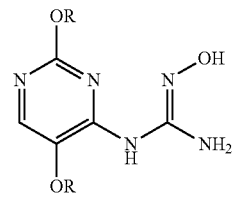

in which R is as previously defined; and
iii) cyclizing the 2,5-dialkoxy-4-hydroxyguanidinylpyrimidine by treating with an alkyl chloroformate to provide the 2-amino-5,8-dialkoxy[1,2,4]triazolo[1,5-c]-pyrimidine (I).

In another embodiment of the invention, the 2,5-dialkoxy-4-cyanoaminopyrimidine can be converted into the corresponding 2-amino-5,8-dialkoxy[1,2,4]-triazolo[1,5-c]-pyrimidine by combining steps ii) and iii) without isolating the 2,5-dialkoxy-4-hydroxyguanidinylpyrimidine.

Another embodiment of the invention comprises a 2,5-dialkoxy-4-cyanoaminopyrimidine of the formula

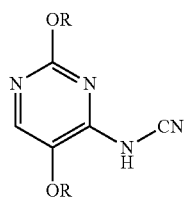

in which R represents $C_1$-$C_4$ alkyl.

A further embodiment of the invention comprises a 2,5-dialkoxy-4-hydroxy-guanidinylpyrimidine of the formula

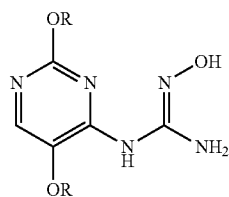

in which R represents $C_1$-$C_4$ alkyl.

The material may exist as a pair of geometric isomers (E and Z), as well as in various tautomeric forms.

DETAILED DESCRIPTION

The term alkyl and derivative terms such as alkoxy, as used herein refer to straight chain or branched chain groups. Typical alkyl groups are methyl, ethyl, propyl, 1-methyl-ethyl, butyl, 1,1-dimethylethyl and 1-methylpropyl. Methyl and ethyl are often preferred.

The present invention concerns the preparation of 2-amino-5,8-dialkoxy[1,2,4]-triazolo[1,5-c]pyrimidines from 4-chloro-2,5-dialkoxypyrimidines.

The first step (a) concerns the conversion of a 4-chloro-2,5-dialkoxypyrimidine (1) in which R represents $C_1$-$C_4$ alkyl to a 2,5-dialkoxy-4-cyanoaminopyrimidine (2). This is accomplished using at least one equivalent of a salt of cyanamide in a polar aprotic solvent. In some embodiments, 1 to about 2.5 molar equivalents of the salt of cyanamide are employed. The salt of cyanamide, in certain embodiments, is an alkali metal salt such as sodium or potassium or an alkaline earth metal salt such as magnesium or calcium. In some embodiments, the salt is sodium hydrogen cyanamide. Exemplary polar aprotic solvents include acetonitrile and amides such as N-methyl-2-pyrrolidinone (NMP). It is also possible to perform the reaction in the presence of additional diluents such as crown ethers and glycol ethers, provided those diluents do not interfere with the desired reaction and are chemically inert to the reactants. The 4-chloro-2,5-dialkoxypyrimidine and the salt of cyanamide are reacted at a temperature from about 0° C. to about 60° C. The product is isolated by conventional techniques, such as by filtration of a precipitated or crystallized material.

In some embodiments, sodium hydrogen cyanamide is suspended in NMP and then treated with the appropriate amount of 4-chloro-2,5-dimethoxypyrimidine. After heating, the reaction mixture is cooled and neutralized with acid to precipitate 2,5-dimethoxy-4-cyanoaminopyrimidine which is collected by filtration and dried.

The second step (b) concerns the conversion of the 2,5-dialkoxy-4-cyanoaminopyrimidine (2) to the 2,5-dialkoxy-4-hydroxyguanidinylpyrimidine (3). This is accomplished using at least an equivalent of either hydroxylamine as a free base or an hydroxylamine salt and a base, such as sodium or potassium carbonate, sodium or potassium hydroxide or a trialkylamine, in a polar solvent. In some embodiments, trialkylamines, such as triethylamine, are utilized as auxiliary bases. In some embodiments, 2 equivalents of hydroxylamine and base are utilized in this reaction. The reactants are, in some embodiments, suspended in a polar solvent and the mixture is stirred at a temperature from about 0° C. to about 80° C. The polar solvent may be either protic or aprotoic. Exemplary protic polar solvents include alcohols such as methanol and exemplary aprotic polar solvents include esters or nitriles such as ethyl acetate or acetonitrile. The product mixture is cooled and treated with water and the 2,5-di-

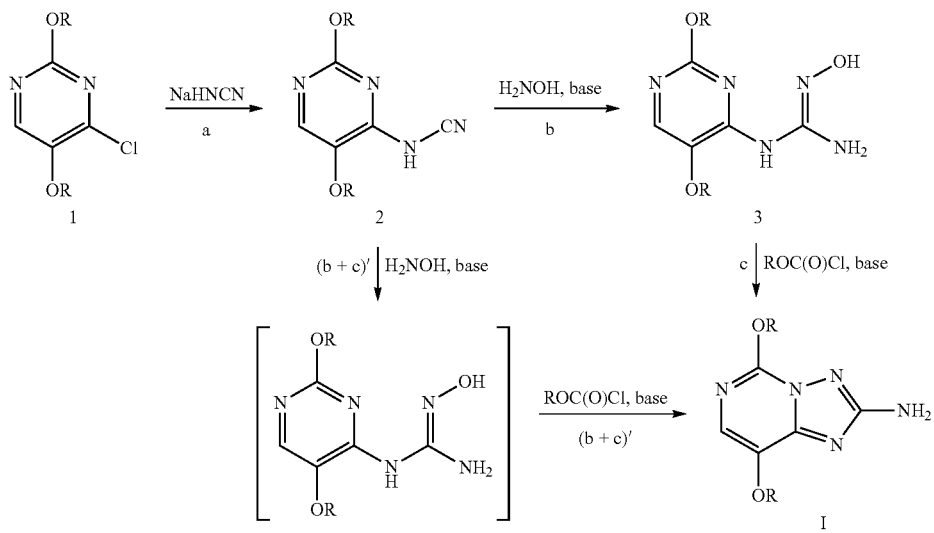

alkoxy-4-hydroxyguanidinylpyrimidine is isolated by conventional techniques, such as collection by filtration and drying. The material may exist as an E/Z isomeric mixture and/or in various tautomeric forms.

In some embodiments, 2,5-dimethoxy-4-cyanoaminopyrimidine and the hydroxylamine salt are slurried in the polar solvent and triethylamine is added. The reaction mixture is stirred at about 45° C. for several hours, treated with water and the 2,5-dimethoxy-4-hydroxyguanidinylpyrimidine is collected by filtration and dried.

The third step (c) concerns the conversion of the 2,5-dialkoxy-4-hydroxyguanidinylpyrimidine (3) to the 2-amino-5,8-dialkoxy[1,2,4]triazolo[1,5-c]pyrimidine (I). This is accomplished using at least an equivalent of a $C_1$-$C_4$ alkyl chloroformate and a base, such as sodium or potassium carbonate, sodium or potassium hydroxide or a trialkylamine, in a polar aprotic solvent. In some embodiments, trialkylamines, such as triethylamine, are utilized as the auxiliary bases. In some embodiments, methyl chloroformate is utilized. In some embodiments, 2 equivalents of alkyl chloroformate and base are utilized in this reaction. The reactants are, in some embodiments, suspended in the polar aprotic solvent and the mixture is stirred at a temperature from about 45° C. to about 100° C. Exemplary polar aprotic solvents include esters or nitriles such as ethyl acetate or acetonitrile. The product mixture is cooled and treated with water and the 2-amino-5,8-dialkoxy[1,2,4]triazolo[1,5-c]pyrimidine (I) is isolated by conventional techniques, such as collection by filtration and drying.

In some embodiments, 2,5-dimethoxy-4-hydroxyguanidinylpyrimidine and methyl chloroformate are slurried in the polar solvent and triethylamine is added. The reaction mixture is stirred at about 80° C. for several hours, treated with water and the 2-amino-5,8-dimethoxy[1,2,4]-triazolo[1,5-c]pyrimidine is collected by filtration and dried.

In some embodiments, steps b and c are combined and the isolation of the 2,5-dialkoxy-4-hydroxyguanidinylpyrimidine (b+c)' is not performed. When combining steps b and c, the reaction needs to be conducted in a polar aprotic solvent such as, for example, ethyl acetate or acetonitrile.

In some embodiments, 2,5-dimethoxy-4-cyanoaminopyrimidine and hydroxylamine hydrochloride are slurried in acetonitrile and triethylamine is added. The reaction mixture is stirred at about 45° C. for several hours and cooled to about 5° C. With external cooling, an additional equivalent of triethylamine is added followed by methyl chloroformate. After briefly stirring at ambient temperature, the reaction mixture is stirred at reflux until completion and treated with water. The solid 2-amino-5,8-dimethoxy[1,2,4]-triazolo[1,5-c]pyrimidine is collected by filtration and dried.

The following examples are presented to illustrate the invention.

EXAMPLES

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

Example 1

Preparation of 2,5-dimethoxy-4-cyanoaminopyrimidine (2)

Step a

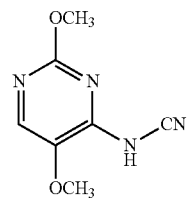

2

To a 100 milliliter (mL) three-neck round bottom flask were added sequentially 7.8 grams (g) (121.53 millimole (mmol)) of sodium hydrogen cyanamide and 34.2 g of N-methyl-2-pyrrolidinone (NMP) in one portion, and the slurry mixture was cooled in an ambient temperature water bath. To this mixture was added 10.0 g (54.99 mmol) of 96% 4-chloro-2,5-dimethoxypyrimidine (1; CDMP) in one portion. The mixture was allowed to stir at ambient temperature (<20° C.). After 65 hours (h), 3.55 g (59.11 mmol) of glacial acetic acid was added in one portion and the internal pot temperature rose from 18° C. to 23° C. This reaction slurry was pipetted over 87.1 g of crushed ice and the ice was allowed to melt. To this mixture was added 10.3 g of sodium chloride. The mixture was allowed to stand until the crushed ice was fully melted. Once melted, the cold slurry was suction filtered and the filter cake was washed with one 10 mL portion of water and then two 20-mL portions of water. The wet cake was isolated to afford 9.39 g (80.2% pure by NMR assay using benzyl acetate) of 2,5-dimethoxy-4-cyanoaminopyrimidine (2) as a light yellow solid mp 164-171° C. in 76% yield; $^1$H NMR (DMSO-$d_6$, 400 MHz) δ 3.72 (s, 3H), 3.94 (s, 3H), 7.46 (s, 1H), 12.48 (br s, ~1H); $^{13}$C NMR (DMSO, 100 MHz) δ 55.21, 56.60, 116.20, 121.8 (br s), 138.9, 153.9, 162.6 (br s).

Example 2

Preparation of 2,5-dimethoxy-4-cyanoaminopyrimidine (2)

Step a

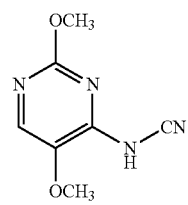

2

To a 100 mL three-neck round bottom flask were added sequentially 7.8 g (121.53 mmol)) of sodium hydrogen cyanamide and then 34.2 g of N-methyl-2-pyrrolidinone (NMP) in one portion, and the slurry mixture was cooled in an ambient temperature water bath. To this mixture was added 10.0 g (54.99 mmol) of 96% 4-chloro-2,5-dimethoxypyrimidine (1; CDMP) in one portion. The mixture was allowed to stir at ambient temperature (<20° C.). After 48 hours (h), 3.78 g (62.95 mmol) of glacial acetic acid was added in one portion and the internal pot temperature rose from 19° C. to 23° C. This reaction slurry was poured over 85 g of crushed ice and the ice was allowed to melt. To this mixture was added 10 g of sodium chloride. The mixture was allowed to stand for 16 minutes (min). Once melted, the cold slurry was suction filtered and the filter cake was washed with two 20-mL portions of water and a final 10 mL water wash. The wet cake transferred to a drying dish and allowed to air dry for 48 h to give 6.78 g (98.8% pure by NMR assay using benzyl acetate) of 2,5-dimethoxy-4-cyanoaminopyrimidine (2) as a light yellow solid in 68% yield. $^1$H and $^{13}$C NMR spectra were identical to that reported in Example 1.

Example 3

Preparation of 2,5-dimethoxy-4-cyanoaminopyrimidine (2)

Step a

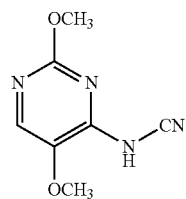

2

4-Chloro-2,5-dimethoxypyrimidine (CDMP; 15 g, 0.086 mol) was dissolved in N-methyl-2-pyrrolidinone (NMP; 62.5 g) at ambient temperature. Sodium hydrogen cyanamide (12.1 g, 2.2 eq) was added all at once, and the mixture was heated to 50° C. with stirring for 2.5 h. The resulting slurry was cooled to 25° C., and 150 mL of water was added. Concentrated hydrochloric acid was added drop-wise until a pH of 5.5 was reached. The thick slurry was filtered and washed twice with 10 mL of water to afford 2,5-dimethoxy-4-cyanoamino-pyrimidine (2) as a white solid (11.83 g, 76% yield).

Example 4

Preparation of 2-amino-5,8-dimethoxy[1,2,4]triazolo[1,5-c]pyrimidine (I)

Step (b+c)'

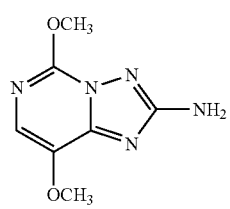

I

To a 25 mL three-neck round bottom flask were added 1.11 g (5.55 mmol) of 90 wt % 2,5-dimethoxy-4-cyanoaminopyrimidine (2), 463 mg (6.66 mmol) of hydroxylamine hydrochloride, and 9.8 g of acetonitrile. To this mixture was added 681 mg (6.72 mmol) of triethylamine in one portion. The reaction mixture was heated to a gentle reflux (~45° C.) for 2 h. The reaction mixture was cooled in an ice water bath to about 5.8° C. at which time an additional 716 mg (7.08 mmol) of triethylamine was added in one portion. To this mixture was added 662 mg (7.01 mmol) of methyl chloroformate in one portion at which time the internal reaction temperature rose from 5.8° C. to 12.1° C. The ice water bath was removed and the mixture was stirred at ambient temperature for 1 h and then at reflux (~76° C.) for about 3 h. The reaction mixture was cooled to ambient temperature and an additional 100 μL of triethylamine was added to adjust the reaction pH to about 7-8. To this mixture was added 11.3 g of water; the mixture was transferred to a 100 mL round bottom flask; and the acetonitrile was removed in vacuo at 60 mm Hg and 30° C. The aqueous slurry was then suction filtered over a medium glass frit and the residue from the flask was transferred with ~2 g of water. After the cake de-liquored, another 1 g displacement water wash was passed through the cake. After suction air drying the cake for 30 min, the mixture was allowed to dry over a nitrogen pad overnight. This afforded 588 mg (~97% pure by liquid chromatography (LC) analysis) of 2-amino-5,8-dimethoxy-[1,2,4]-triazolo[1,5-c]pyrimidine (I) as a light yellow solid in 52.8% yield from starting 2,5-dimethoxy-4-cyanoaminopyrimidine (2). $^1$H NMR (DMSO-d$_6$, 400 MHz) δ 3.90 (s, 3H), 4.06 (s, 3H), 6.28 (br s, 2H), 7.48 (s, 1H); $^{13}$C NMR (DMSO-d$_6$, 100 MHz) δ 55.37, 57.04, 123.07, 138.60, 143.73, 148.50, 166.02.

Example 5

Preparation of 2,5-dimethoxy-4-hydroxyguanidnylpyrimidine (3)

Step b

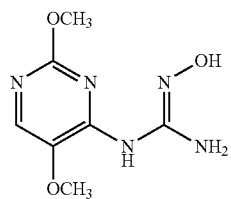

3

2,5-Dimethoxy-4-cyanoaminopyrimidine (CDMP; 2; 10 g, 0.055 mol) and hydroxylamine hydrochloride (5.09 g, 1.33 eq) were dispersed in methanol (60 ml). Triethylamine (7.59 g, 1.36 eq) was added and the slurry was heated to 45° C. with stirring. After 3 h at 45° C., the slurry was cooled to room temperature and 60 mL of water was added followed by a 20 min digestion period. The slurry was filtered and the solid was dried to constant weight to afford 2,5-dimethoxy-4-hydroxyguanidnylpyrimidine (3) as a light tan solid (8.70 g, 74%). mp 159-168° C. (dec); $^1$H NMR (DMSO-d$_6$, 400 MHz) δ 3.78 (s, 3H), 3.82 (br s, 3H), 6.58 (br s, 2H), 7.85 (s, 1H), 8.66 (br s, 2H); $^{13}$C NMR (DMSO-$d_6$, 100 MHz) δ 54.01, 56.78, 136.51 (br s), 138.20, 150.50 (br s), 153.42 (br s), 157.69.

Example 6

Preparation of 2-amino-5,8-dimethoxy[1,2,4]triazolo [1,5-c]pyrimidine (I)

Step c

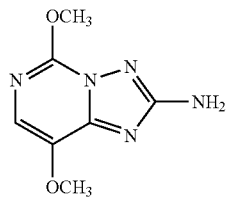

2,5-Dimethoxy-4-hydroxyguanidnylpyrimidine 3 (6 g, 0.028 mol) was dispersed in ethyl acetate (24 g). Ethyl chloroformate (3.7 g, 0.034 mol) was added to the slurry followed immediately by triethylamine (3.4 g, 0.034 mol). The slurry temperature rose to 48° C. and was further adjusted to 78° C. with applied heat. The viscosity of the slurry thinned and the solids went from white to a cream color as the slurry was heated. The conversion to I was slow, so water (20 g) was added at the 3 h mark. Water addition did not increase the rate of reaction, but after 9 h, the slurry contained 84.4% product I by LC analysis. The mixture was cooled to 22° C., filtered, and the wet-cake was washed with water (15 g). Drying afforded the 2-amino-5,8-dimethoxy[1,2,4]-triazolo[1,5-c] pyrimidine (I) as a cream colored solid (3.57 g) that was 91.9% pure by LC area percent. The yield was 60% based on 3.

What is claimed is:

1. A process for the preparation of 2-amino-5,8-dialkoxy [1,2,4]-triazolo[1,5-c]-pyrimidines of the formula (I),

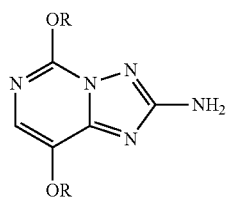

wherein R is $C_1$-$C_4$ alkyl
comprising:
i) contacting a 4-chloro-2,5-dialkoxypyrimidine of the formula

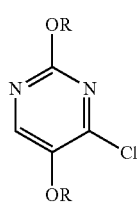

wherein R is as previously defined with a salt of cyanamide in a polar aprotic solvent to provide a 2,5-dialkoxy-4-cyanoaminopyrimidine of the formula

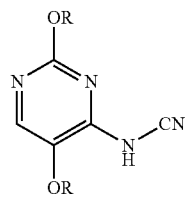

in which R is as previously defined;
ii) contacting the 2,5-dialkoxy-4-cyanoaminopyrimidine with either hydroxylamine as a free base or hydroxylamine salt in the presence of a base to provide a 2,5-dialkoxy-4-hydroxyguanidinylpyrimidine of the formula

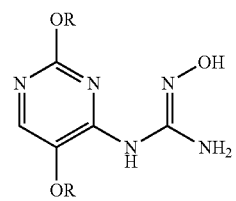

wherein R is as previously defined; and
iii) cyclizing the 2,5-dialkoxy-4-hydroxyguanidinylpyrimidine by treating with an alkyl chloroformate to provide the 2-amino-5,8-dialkoxy[1,2,4]-triazolo[1,5-c] pyrimidine.

2. The process of claim 1, wherein R is $CH_3$.

3. The process of claim 1, wherein the 2,5-dialkoxy-4-hydroxyguanidinyl-pyrimidine of step ii) is used without isolation to prepare the 2-amino-5,8-dialkoxy[1,2,4]-triazolo[1, 5-c]pyrimidine in step iii).

4. The process of claim 1, wherein the salt of cyanamide is an alkali metal salt or alkaline earth metal salt.

5. The process of claim 1, wherein the salt of cyanamide is sodium hydrogen cyanamide.

6. The process of claim 1, wherein the polar aprotic solvent of (i) is acetonitrile or N-methyl-2-pyrrolidinone.

7. The process of claim 1, wherein (i) is performed at a temperature of from about 0° C. to about 60° C.

8. The process of claim 1, wherein the free base of hydroxylamine salt of (ii) is a sodium carbonate, potassium carbonate, sodium hydroxide, potassium hydroxide, or a trialkylamine salt.

9. The process of claim 1, wherein (ii) is performed in a polar solvent.

10. The process of claim 9, wherein the solvent is methanol, ethyl acetate, or acetonitrile.

11. The process of claim 1, wherein (ii) is performed at a temperature of from about 0° C. to about 80° C.

12. The process of claim 1, wherein the alkylchloroformate of (iii) is a methyl chloroformate.

13. The process of claim 1, wherein (iii) is performed in the presence of a base.

14. The process of claim 13, wherein the base is sodium carbonate, potassium carbonate, sodium hydroxide, potassium hydroxide, or triethylamine.

15. The process of claim 1, wherein (iii) is performed at a temperature of from about 45° C. to about 100° C.

16. The process of claim 1, wherein (iii) is performed in a polar aprotic solvent.

17. The process of claim 16, wherein the solvent is ethyl acetate or acetonitrile.

18. A process for the preparation of 2-amino-5,8-dialkoxy [1,2,4]-triazolo[1,5-c]-pyrimidines of the formula (I),

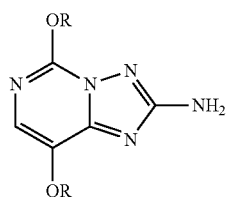

wherein R is $C_1$-$C_4$ alkyl comprising:
cyclizing a 2,5-dialkoxy-4-hydroxyguanidinylpyrimidine of the formula

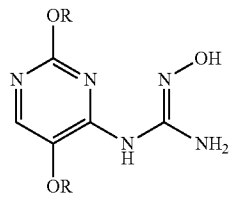

wherein R is as previously defined;
by treating with an alkyl chloroformate to provide the 2-amino-5,8-dialkoxy[1,2,4]-triazolo[1,5-c]pyrimidine.

19. The process of claim 18, wherein the 2,5-dialkoxy-4-hydroxyguanidinylpyrimidine is formed by contacting a 2,5-dialkoxy-4-cyanoaminopyrimidine of the formula

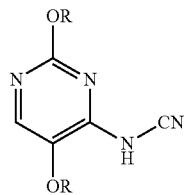

in which R is as previously defined
with either hydroxylamine as a free base or hydroxylamine salt in the presence of a base to provide a 2,5-dialkoxy-4-hydroxyguanidinylpyrimidine.

20. A compound of the formula

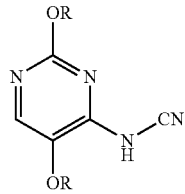

in which R represents $C_1$-$C_4$ alkyl.

21. A compound of the formula

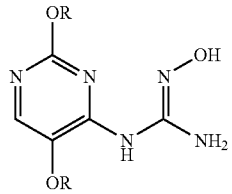

in which R represents $C_1$-$C_4$ alkyl.

* * * * *